United States Patent [19]
Choi et al.

[11] Patent Number: 5,662,092
[45] Date of Patent: Sep. 2, 1997

[54] SPHYGMOMANOMETER AND METHOD FOR CONTROLLING OPTIMUM PRESSURIZATION AND MINUTE EXHAUSTION WHILE MEASURING BLOOD PRESSURE

[75] Inventors: Tae-Young Choi, Seoul; Si-Chul Lee; Yong-Bum Kim, both of Kyungki-do, all of Rep. of Korea

[73] Assignee: Sein Electronics Co., Ltd., Kyungki-do, Rep. of Korea

[21] Appl. No.: 505,603

[22] Filed: Jul. 21, 1995

[30]    Foreign Application Priority Data

Jul. 27, 1979 [KE] Kenya ........................... 94-18259
Aug. 31, 1994 [KR] Rep. of Korea ................ 94-21816

[51] Int. Cl.$^6$ ........................................... A61B 5/02
[52] U.S. Cl. ..................... 128/680; 128/672; 128/677
[58] Field of Search ........................... 128/677–685, 128/687, 672

[56] References Cited

U.S. PATENT DOCUMENTS

| | | | |
|---|---|---|---|
| 4,458,690 | 7/1984 | O'Conner et al. | 128/680 |
| 4,567,899 | 2/1986 | Kamens et al. | 128/680 |
| 5,280,790 | 1/1994 | Brooks | 128/682 |
| 5,337,751 | 8/1994 | Newel et al. | 128/682 |
| 5,467,772 | 11/1995 | Souma | 128/682 |

FOREIGN PATENT DOCUMENTS 9324242  11/1993  Rep. of Korea .

*Primary Examiner*—Lee S. Cohen
*Assistant Examiner*—Bryan K. Yarnell
*Attorney, Agent, or Firm*—Christie, Parker & Hale, LLP

[57]    ABSTRACT

A sphygmomanometer for controlling an optimum pressurization and minute exhaustion comprises a cuff which is wrapped around the upper arm of a subject for compressing the brachial artery. The cuff is pressurized with an air pump controlled by a microcontroller. The microcontroller is programmed to terminate the pressurization process at the point the systolic pressure is detected. The microcontroller further controls the exhaustion of air by switching a solenoid valve on and off and thereby negate the need for a costly minute exhaust valve. During the pressurization and depressurization process, pressure waves are transmitted from the brachial artery to a sensor where they are converted to an electrical signal for processing by the microcontroller. The microcontroller computes the systolic and diastolic pressure and routes the data to a display for visual readout.

8 Claims, 5 Drawing Sheets

SPHYGMOMANOMETER AND METHOD FOR CONTROLLING OPTIMUM PRESSURIZATION AND MINUTE EXHAUSTION WHILE MEASURING BLOOD PRESSURE

BACKGROUND OF THE INVENTION (1) Field of Invention

The present invention relates to health care equipment and more specifically to a sphygmomanometer and method for controlling optimum pressurization and minute exhaustion of air while measuring blood pressure.

(2) Description of the Prior Art

A sphygmomanometer is an apparatus for measuring the blood pressure of a subject. The sphygmomanometer comprises a cuff which is wrapped around the upper arm. The cuff is inflated by a pump which provides sufficient pressure to compress the brachial artery in the upper arm. A pulsation transmitted from the artery to the cuff is processed by an electrical circuit to determine the blood pressure of a patient.

A portable sphygmomanometer is described in Korean Pat. No. 93-24242 filed on Nov. 15, 1993, entitled "A portable sphygmomanometer worked by hand".

Figure 1:
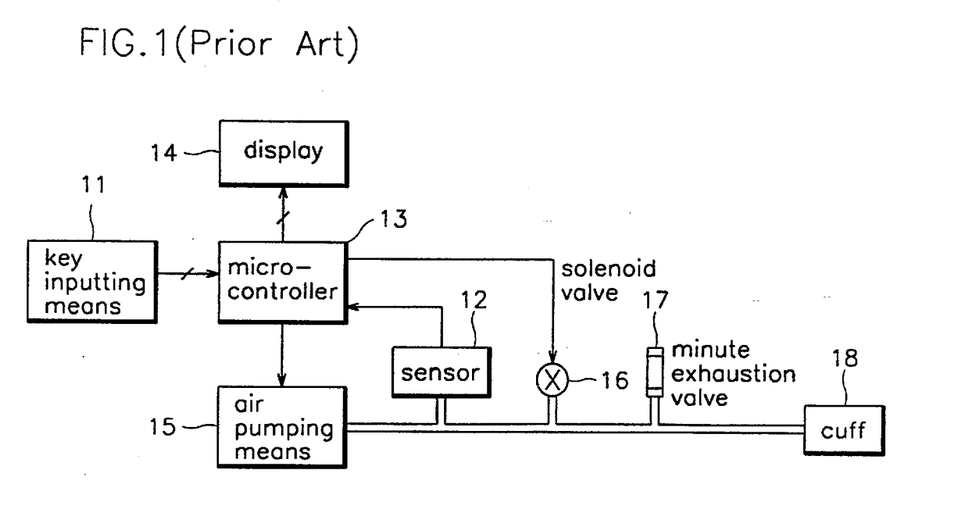
FIG. 1 is a block diagram of a conventional sphygmomanometer.

A conventional sphygmomanometer is shown in FIG. 1 which includes a key inputting means 11 connected to a microcontroller 13, an air pumping means 15 connected to the output of a the microcontroller 13, a display 14 connected to second output of the microcontroller 13, and a sensor 12, a solenoid valve 16, a cuff 18, and a minute exhaustion valve 17 which are coupled to the air pumping means 15 output through an air duct. The output of the sensor 12 is fed back to the input of the microcontroller 13. The solenoid valve 16 is controlled by a third output of the microcontroller 13.

In operation, a user inputs an operating command with the key inputting means 11 causing the microcontroller 13 to activate the air pumping means 15 to pressurize the air duct. The air pressure is transmitted to the sensor 12, the solenoid valve 16, the cuff 18, and the minute exhaustion valve 17 through the air duct.

During the pressurization process, the microcontroller 13 causes the solenoid valve 16 to remain closed so that the majority of air flow is directed to the cuff 18 wrapped around the upper arm of the subject. During the pressurization process, the sensor 12 begins detecting pressure waves transmitted from the brachial artery and converts them into electrical signals for processing by the microcontroller 13. The pressurization process continues until the processor detects no further pressure waves from the sensor at which point the pressure in the cuff indicated by the sensor is read into memory of the microcontroller 13. This pressure represents the systolic pressure of the subject.

Figure 2:
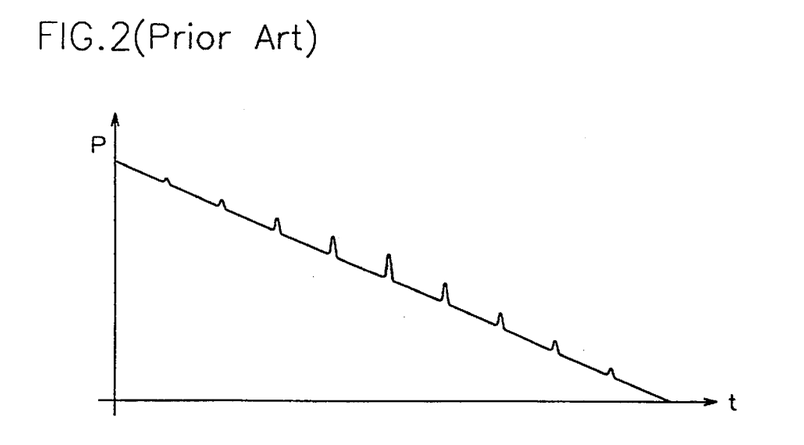
FIG. 2 is a pressure wave graph of a conventional sphygmomanometer.

Once the pressurization process is terminated, the depressurization of the air duct occurs by exhausting the air through the minute exhaustion valve 17. Similarly to the pressurization process, the sensor 12 converts the pressure waves from the brachial artery to an electrical signal for processing by the microcontroller 13 until no further pressure waves are detected at which time the pressure in the cuff is read in the memory. This pressure represents the diastolic pressure. The microcontroller 13 outputs data to a display for a visual readout of the systolic and diastolic pressure. Upon displaying the results, the microcontroller causes the air duct to completely depressurized by opening the solenoid valve 16. A graphical representation of the pressure waves during the depressurization process is shown in FIG. 2.

With the recent trend toward improved health care, a demand has arisen for portable sphygmomanometers which can be operated by an individual. A portable sphygmomanometer is described in Korean Pat. No. 93-24242 filed on Nov. 15, 1993, entitled "A portable sphygmomanometer worked by hand." However, to accommodate the commercialization of portable sphygmomanometers, the size and cost of these devices must be reduced.

One obstacle to meeting these commercial objectives is that a conventional sphygmomanometer uses an expensive rolling pump with a large air tank to attenuate pressure fluctuations that would otherwise result in inaccurate blood pressure readings. Moreover, the pump typically generates excessive pressure than that required and therefore results in unnecessary power consumption.

Another obstacle to commercialization of the portable sphygmomanometer is that the minute exhaustion valve is a precision part requiring a complicated manufacturing process to satisfy the standardized exhaustion deviation and thereby contributes to the production costs of the sphygmomanometer. If the exhaustion rate is not within the standardized deviation, according to an arm thickness of the object, the quality and size of the cuff, the pressure fluctuations of the device, the pressurization of the cuff, and heart rate of the patient, the accuracy of the blood pressure measurement will be reduced.

SUMMARY OF THE INVENTION

An embodiment of the present invention is a sphygmomanometer and method for controlling optimum pressurization and minute exhaustion of air while measuring a blood pressure that is capable of solving the problems in the existing art. In one embodiment of the invention, the sphygmomanometer is an air pump for pressurizing an air duct. Preferably, an air tank is connected to the output of the air pump for attenuating pressure fluctuations in the air duct. A buffer may also be used in conjunction with the air tank to control pressurization. A solenoid valve is provided for exhausting the air in the air duct. A cuff is connected to the air duct for wrapping around the upper arm of the subject to compress the brachial artery. The pulsation of the brachial artery causes pressure waves in the air duct which are detected by a sensor. The sensor converts the pressure of the air duct to an electrical signal for processing by a microcontroller. The microcontroller controls the pressurization and depressurization of the air duct and computes the blood pressure in response to the electrical signal from the sensor. The microcontroller provides an output for driving a display for a visual readout of the blood pressure. A key input is provided for user control.

To initiate operation, a battery is installed into the sphygmomanometer which causes the solenoid valve to the air duct to open. The microcontroller initializes internal memory and enters a power saving mode until a power-on command from the key input is detected. Once a power-on command signal is detected, the microcontroller waits for a subsequent input from the key input. In the event that a subsequent input is not detected within a predetermined time after the actuation of the power-on command, the microcontroller re-enters the power saving mode. In the event that a subsequent input is detected during the prescribed time, the solenoid valve is closed and the air duct is pressurized by the air pump until a systolic pressure is detected. The microcontroller computes a diastolic pressure by controlling the minute exhaustion of the air duct. Once the systolic and diastolic pressures are computed, the microcontroller outputs the data to a display for visual readout, depressurizes the air duct by opening the solenoid valve and turns off the sphygmomanometer.

An attractive feature of one embodiment of the present invention is that the microcontroller terminates the pressurization of the air duct at the systolic pressure to avoid excessive pressurization that cause discomfort to the subject being tested.

An advantage of an embodiment of the present invention is that by controlling the solenoid valve for minute exhaustion with the microcontroller, a constant rate of depressurization can be maintained irrespective of the air pressure and the arm thickness and thereby improves the accuracy of the measurement. Moreover, production costs are reduced since the sphygmomanometer can be made without a complex and costly minute exhaustion valve.

BRIEF DESCRIPTION OF THE DRAWINGS

These and other features, aspects, and advantages of the present invention will become understood with regard to the following description, appended claims, and accompanying drawings where:

DETAILED DESCRIPTION OF THE PREFERRED EMBODIMENTS

Figure 3:
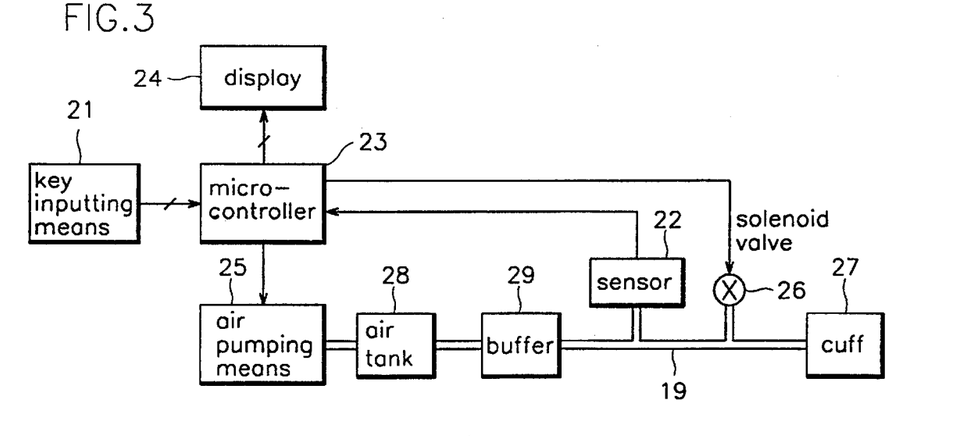
FIG. 3 is a block diagram of sphygmomanometer for controlling an optimum pressurization in accordance with a preferred embodiment of the present invention.

As shown in FIG. 3, according to a preferred embodiment of the present invention, a sphygmomanometer having an optimum pressurization controlling function includes an air duct 19; an air pump or pumping means 25 for pressurizing the air duct; and air tank 28 connected to the output of the air pumping means 25; a buffer 29 connected to the output of the air tank 28; a sensor 22, a solenoid valve 26, and a cuff 27 connected to the air duct 19; a microcontroller 23 responsive to an actuation of a control switch or key inputting means 21 and the sensor 22 for generating control signals therefrom to control the air pumping means 25 and the solenoid valve 26. The microcontroller 23 further provides a computed blood pressure to a display 24 for visual presentation to a user.

Figure 4:
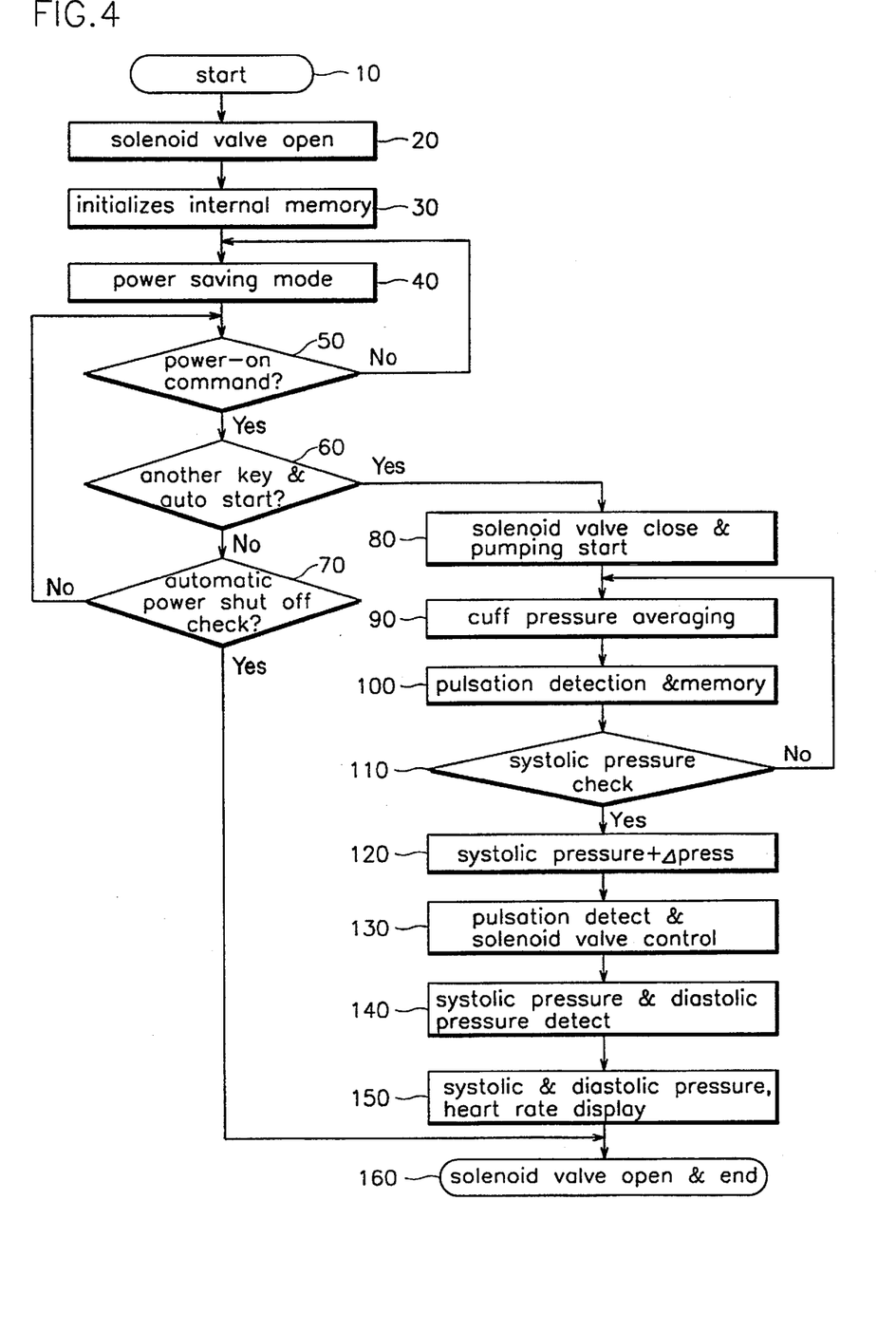
FIG. 4 is an operation flow chart of a method for controlling a sphygmomanometer for optimum pressurization in accordance with a preferred embodiment of the present invention.

The pressurization of the sphygmomanometer is implemented by a control program (not shown in FIG. 3) stored in the microcomputer. The control program is illustrated in a flow diagram in FIG. 4. Referring to FIGS. 3 and 4, the control program is initiated by applying power to the sphygmomanometer by inserting a battery (nor shown). Upon the application of power from the inserted battery, the microcontroller causes the solenoid valve to open 20. Once the solenoid valve is open, the microcontroller initializes internal memory 30, enters into a power saving mode 40, and waits for a power-on command 50 from the key inputting means. Once a power-on command is detected, the microcontroller enters into a wait mode for a subsequent input from the key inputting means 60. In the event that a subsequent input from the key inputting means is not detected by the microcontroller within a predetermined time after the power-on command, a power-off command is internally generated by the microcontroller 70. In the event that the microcontroller detects a subsequent input from the key inputting means within the prescribed time period, the microcontroller causes the solenoid valve to close and the air pumping means to begin pressurizing the air duct 80. The microcontroller begins calculating the average pressure applied to the cuff 90 and uses this data to detect pressure waves generated by the brachial artery of a subject. Data representative of the pressure waves is captured in memory (not shown) of the microcontroller 100. The pressurization of the air duct continues until a systolic pressure is detected 110 whereby the air duct is slightly pressurized further 120 before the air pumping means is shut off by the microcontroller. Once the air pumping means is shut off, the depressurization of the air duct begins. The microcontroller determines the rate of depressurization by controlling the solenoid valve 130. The microcontroller further detects pressure waves from the brachial artery until a diastolic pressure is detected 140. The microcontroller presents the systolic pressure, the detected diastolic pressure, and a heart rate to the display 150. Once the systolic and diastolic pressure is calculated by the microcontroller and displayed, the air duct is rapidly depressurized causing the remainder of the air to be exhausted through the solenoid valve 160.

In operation, power is applied to the sphygmomanometer which causes the microcontroller to perform the control program shown in FIG. 4. Once power is applied, the microcontroller 23 outputs a signal to the solenoid valve 26 causing it to open.

Next, the microcontroller 23 initializes internal memory and enters a power-saving mode which reduces power consumption. In the power-saving mode, the microcontroller 23 determines whether a signal inputted from the key inputting means 21 is a power-on command. Once a power-on command is detected, the microcontroller enters into a wait mode for a subsequent input from the key inputting means 21. In the event that a subsequent input from the key inputting means 21 not detected by the microcontroller within a predetermined time after the power-on command, a power-off command is internally generated by the microcontroller 23 and the microcontroller 23 re-enters the power saving mode. In the event that the microcontroller 23 detects a subsequent input from the key inputting means within the prescribed time period, the microcontroller 23 causes the solenoid valve 26 to close and the air pumping means 25 to begin pressurizing the air duct 19.

The air pressure generated from the air pumping means 25 is transmitted to the air tank 28 through the air duct 19. The output of the air tank 28 is transmitted to the buffer 29 through the air duct 19. The output of the buffer is transmitted to the sensor 22, the solenoid valve 26, and the cuff 27, through the air duct 19. during the air pressurization of the air duct, the microcontroller 23 causes the solenoid valve 26 to remain closed so that the majority of air flow is directed to the cuff 27 wrapped around the upper arm of the subject. During this process, the sensor 22 converts the pressure waves transmitted by the pulsation of the brachial artery into an electrical signal for processing by the microcontroller 23. The microcontroller computes the average value of the air pressure in the air duct 19 and uses this data to detect the pressure waves superimposed thereon. The data representative of the pressure waves is stored in internal memory.

Figure 5:
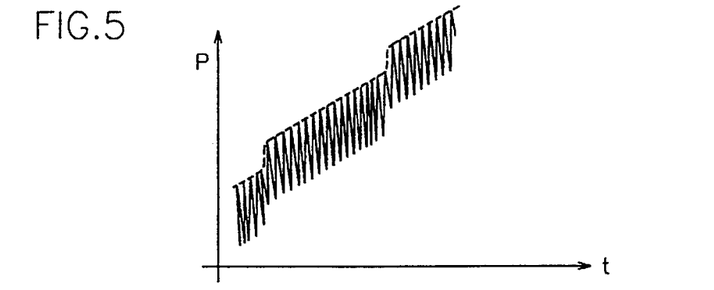
FIG. 5 is a pressure wave graph of a sphygmomanometer for controlling an optimum pressurization during pressurization without a buffer and air tank in accordance with a preferred embodiment of the present invention.
Figure 6:
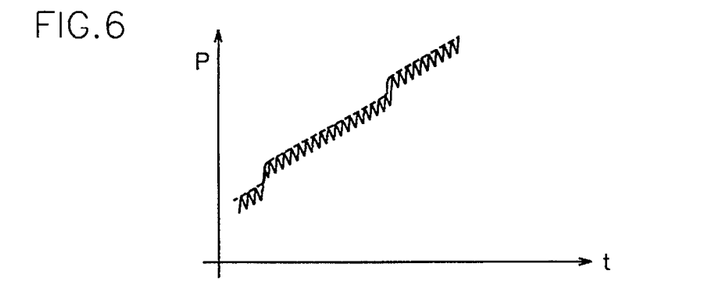
FIG. 6 is a pressure wave graph of a sphygmomanometer for controlling an optimum pressurization during pressurization without a buffer in accordance with a preferred embodiment of the present invention.
Figure 7:
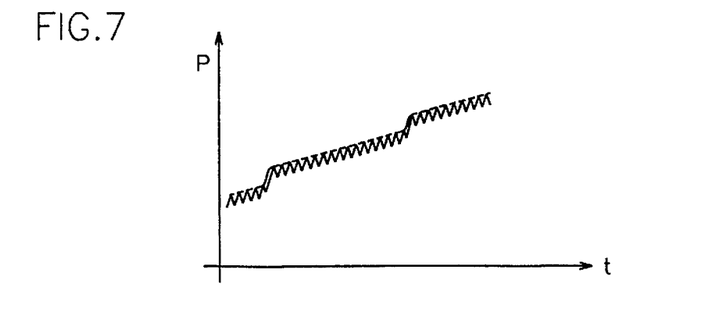
FIG. 7 is a pressure wave graph of a sphygmomanometer for controlling an optimum pressurization during pressurization with both the buffer and air tank in accordance with a preferred embodiment of the present invention.

FIGS. 5 to 7 illustrate the pressure waves applied to the sensor 12 during the pressurization process. As shown in FIG. 7, as compared with FIGS. 5 and 6, the pressure fluctuations in the air duct 19 are attenuated by using a shock absorbing air tank 28 made of soft rubber. The attenuation of the pressure fluctuations enhances the sensitivity of the sensor for detecting pressure waves from the brachial artery.

The microcontroller 23 continues to detect and store data representative of the pressure waves until a systolic pressure is achieved. Once the systolic pressure is achieved, the microcontroller 23 promptly terminates the pressurizing process by outputting a signal to the air pumping means 25 causing it to shut off. The advantage of controlling the pressurization of the air duct 19 with the microcontroller 23 is that excessive pressurization of the cuff 27 can be avoided by stopping pressurization at or just above systolic pressure, thereby eliminating any unnecessary discomfort to the subject being tested.

The microcontroller 23 causes the air duct to depressurize by controlling the solenoid valve 16. During the depressurization process, the pressure waves are detected and stored in memory of the microcontroller 23 until a diastolic pressure is obtained. Once the systolic and diastolic blood pressure is determined, the microcontroller 23 routes the systolic pressure, diastolic pressure and heart rate to the display 24 and causes rapid depressurization of the air duct by opening the solenoid valve 26.

Figure 8:
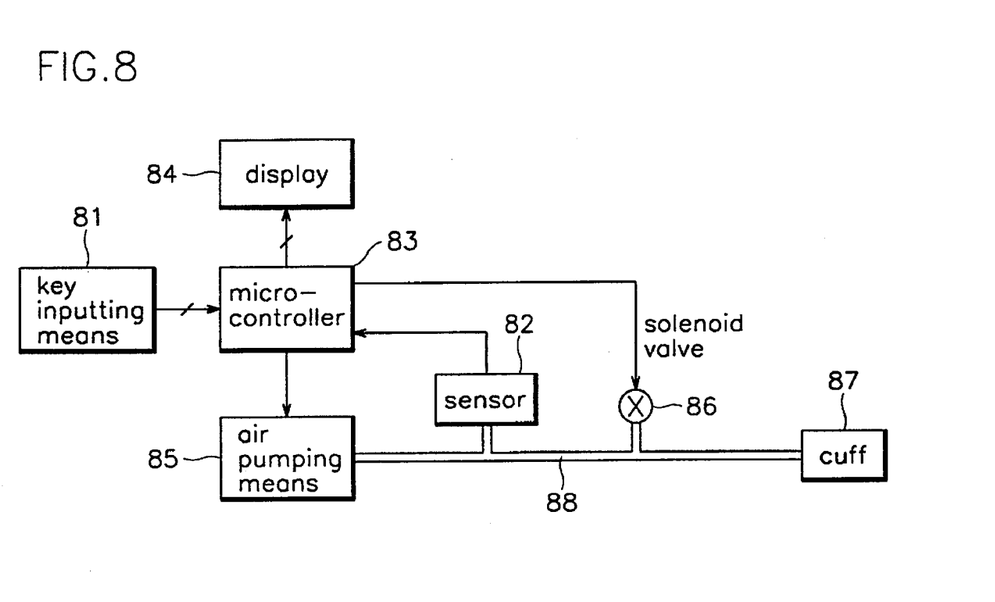
FIG. 8 is a block diagram of a sphygmomanometer having a minute exhaustion controlling function in accordance with a preferred embodiment of the present invention.

Turning to FIG. 8, according to a preferred embodiment of the present invention, a sphygmomanometer having a minute exhaustion controlling function includes a key inputting means 81 connected to a microcontroller 83; an air pumping means 85 connected to an output microcontroller 83; a sensor 82, a solenoid valve 86, and a cuff 87 connected to the air duct 88; and a display 84 driven by an second output of the microcontroller 83.

Figure 9:
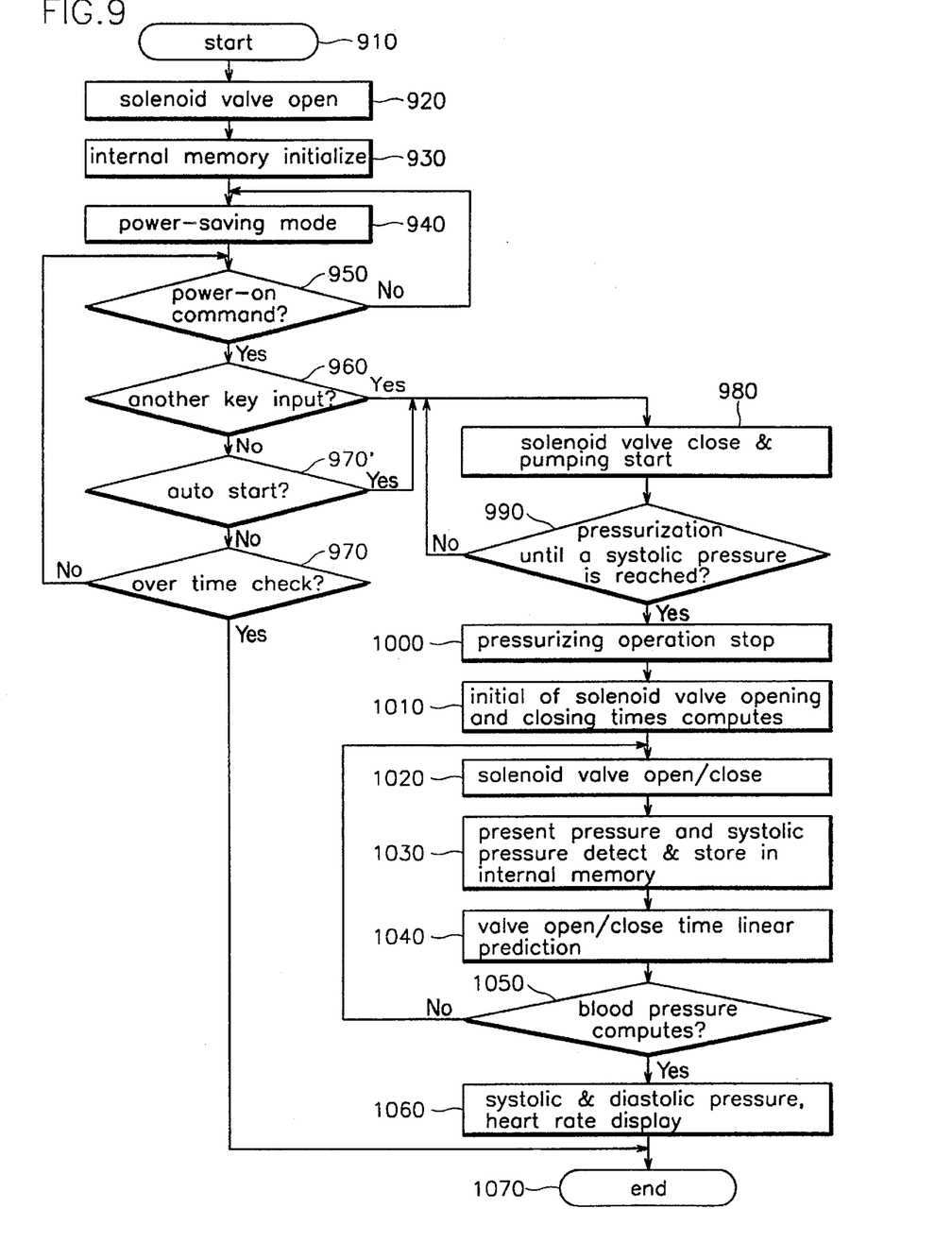
FIG. 9 is an operation flow chart of a method for controlling a minute exhaustion function of a sphygmomanometer in accordance with a preferred embodiment of the present invention.

The minute exhaustion controlling function of the sphygmomanometer is implemented by a control program (not shown in FIG. 8) stored in the microcontroller. A flow diagram of the control program is shown in FIG. 9. Referring to FIGS. 8 and 9, the control program is initiated by applying power to the sphygmomanometer by inserting a battery 910. Upon application of power, the microcontroller causes the solenoid valve to open 920. Once the solenoid valve is open, the microcontroller initializes internal memory (not shown) 930, enters into a power saving mode 940 and waits for a power-on command 950 from the key inputting means. Once a power-on command is detected, the microcontroller enters into a wait mode for a subsequent input from the key inputting means 960. In the event that a subsequent input from the key inputting means is not detected by the microcontroller within a predetermined time after the power-on command, a power-off command is internally generated by the microcontroller 970. An auto start function may programmed into the microcontroller. which initiates operation of the sphygmomanometer upon detection of the power-on command 970'. In the absence of an auto start function, upon detecting a subsequent input from the key inputting means within the prescribed time period, the microcontroller causes the solenoid valve to closed and the air pumping means to begin pressurizing the air duct 980. The pressurization continues until the air duct reaches a systolic pressure 990 upon where the air pumping means is shut off 1000. The depressurization process begins with the microcontroller computing the opening and closing times of the solenoid valve required for minute exhaustion 1010 and then alternatively turing on or off the solenoid valve in accordance therewith 1020. During the depressurization process, the microcontroller begins calculating the average pressure in the air duct and uses this data to detect pressure waves superimposed thereon from the brachial artery. Data representative of the detected pressure waves are stored in memory 1030. The microcontroller continues to adjust the time the solenoid valve remains open and closed to maintain a linear depressurization of the air duct 1040. The microcontroller continues to depressurize the air duct until a diastolic pressure is detected 1050 at which time it presents a systolic and diastolic pressure to the display 1060.

In operation, power is applied to the sphygmomanometer which causes the microcontroller 83 to perform the control program shown in FIG. 9. Once power is applied, the microcontroller 83 outputs a signal to the solenoid valve 86 causing it to open.

Next, the microcontroller 83 initializes the internal memory and enters a power saving mode which reduces power consumption. In the power saving mode, the microcontroller 83 determines whether a signal inputted from the key inputting means 81 is a power-on command. Once a power-on is detected, the microcontroller 83 searches internal memory for an auto start function which would cause the sphygmomanometer to begin operating in the absence of a subsequent command from the key inputting means 81. In the event that an auto start feature is not provided for, the microcontroller 83 enters into a wait mode for a subsequent input from the key inputting means 81. In the event that a subsequent input from the key inputting means 81 is not detected by the microcontroller 83 within a predetermined time after the power-on command, a power-off command is internally generated by the microcontroller 83 and the microcontroller 83 re-enters the power saving mode. In the event that the microcontroller 83 detects a subsequent input from the key inputting means 81 within the prescribed time period, the microcontroller 83 causes the solenoid valve 86 to closed and the air pumping means 85 to begin pressurizing the air duct 88. The air pressure generated from the air pumping means 85 is transmitted to the sensor 82, the solenoid valve 86, and the cuff 87, through the air duct 88. During the air pressurization of the air duct, the microcontroller 83 causes the solenoid valve 86 to remain closed so that the majority of the air flow is directed to the cuff 87 wrapped around the upper arm of the subject. During this process, the sensor 82 converts the pressure waves transmitted by the pulsation of the brachial artery into an electrical signal for processing by the microcontroller 83. The microcontroller 83 computes the average value of the air pressure in the air duct 19 and uses this data to detect the pressure waves. Data representative of the pressure waves is stored in internal memory. The microcontroller 83 continues to detect and store data representative of the pressure waves until a systolic pressure is achieved. Once the systolic pressure is achieved, the microcontroller 83 terminates the pressurizing process by outputting a signal to the air pumping means 85 causing it to shut off.

Figure 10:
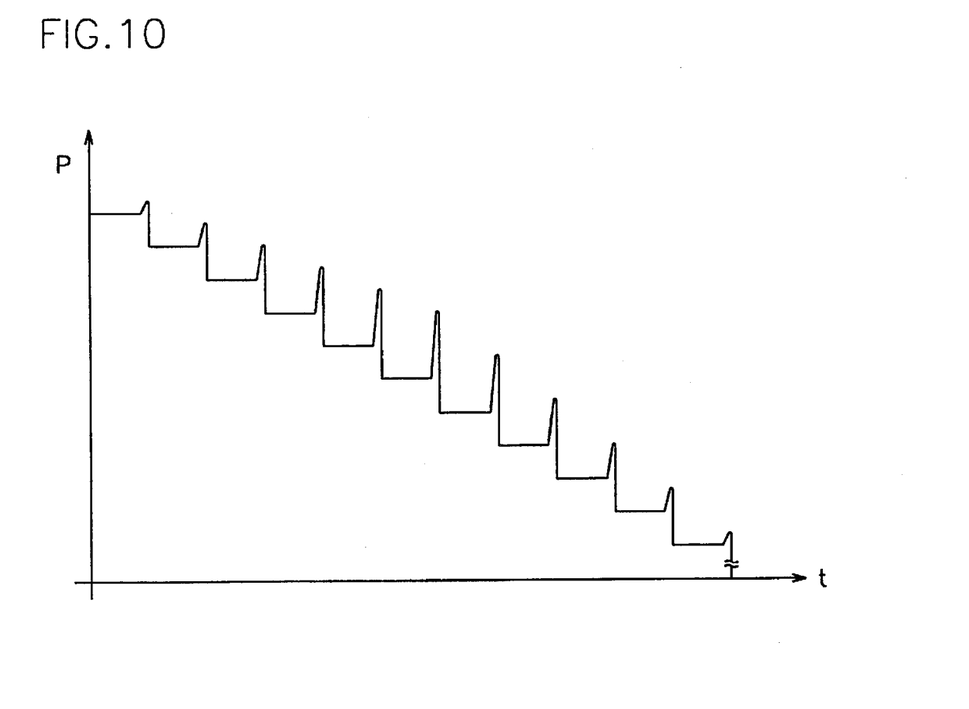
FIG. 10 is a pressure wave graph of a sphygmomanometer having a minute exhaustion controlling function.

Next, the microcontroller 83 computes the initial opening and closing times for the solenoid valve 86 for optimum minute exhaustion, and minutely exhausts the air by alternatively turning on or off the solenoid valve 86. During the depressurization process, the pressure waves are detected by the sensor 82 and converted to an electrical signal for processing by the microcontroller 83. The sensor input is illustrated in FIG. 10 where the pressure waves are superimposed on the average pressure in the air duct 88. Similarly to the pressurization process, the microcontroller 83 computes the average pressure and uses this data to detect the pressure waves. Data representative of the pressure waves is stored in the internal memory.

Next, the microcontroller 83 corrects the opening and closing times of the solenoid valve 86 by means of a linear prediction which is derived from a minute exhaustion quantity's distribution prior to the present pressure. The solenoid valve 86 opening and closing times are computed by the linear prediction by an experiment as well as a theory.

After correcting the solenoid valve 86 opening and closing times, the microcontroller 86 computes the blood pressure and presents both the systolic pressure and the diastolic pressure to the display 84 for a visual readout.

After the microcontroller 83 computes the systolic and diastolic pressure, the air duct 88 is rapidly depressurized by the microcontroller 86 which causes the solenoid valve 86 to open and the sphygmomanometer from further operating.

The disclosure of attached Korean Patent Application No. 94-18259 filed on Jul. 27, 1994, and No. 94-21816 filed on Aug. 31, 1994, are incorporated fully herein by reference. Priority of these Korean applications is claimed.

In a preferred embodiment of the present invention, an exhaust rate of 2–3 mmHg per heart beat irrespective of variation of the air pressure, arm thickness, and quality and size of the cuff can be achieved and thereby improve the precision of the measurement. Also, a manufacturer can produce a sphygmomanometer without a minute exhaustion valve thereby reducing cost of production. This sphygmomanometer may be embodied in other specific forms and used with a variety of health care devices without departing from the spirit or essential attributes of the present invention. It is therefore desired that the present embodiment be considered in all respects as illustrative as illustrative and not restrictive, reference being made to the appended claims than the foregoing description to indicate the scope of the invention.

What is claimed is:

1. A sphygmomanometer for controlling an optimum pressurization, comprising:

a cuff for compressing an arm of a subject;

an air pumping means having an output for pressurizing said cuff;

an air tank connected to the output of said air pumping means for attenuating pressure fluctuations produced by said air pumping means;

a solenoid valve for depressurizing said cuff;

a sensor for converting pressure in said cuff to an electrical signal, said pressure being representative of a pressure exerted on said cuff by an artery of the arm;

a microcontroller comprising means for controlling said solenoid valve, and means for computing a blood pressure in response to said electrical signal from said sensor;

a display connected to said microcontroller for displaying the calculated blood pressure; and a key inputting means for controlling said microcontroller.

2. A sphygmomanometer for controlling an optimum pressurization of claim 1, further comprising a buffer connected to an output of said air tank for controlling said pressurization of said cuff.

3. A sphygmomanometer for controlling an optimum pressurization of claim 1 or claim 2 wherein said air tank comprises rubber.

4. A sphygmomanometer for controlling an optimum pressurization of claim 1 or claim 2 wherein said means for controlling said solenoid valve produces a minute exhaustion of 2–3 mmHg per heart beat.

5. A method of controlling a sphygmomanometer from a key inputting means for optimum pressurization comprising the steps of:

inserting a battery into said sphygmomanometer;

opening a solenoid valve coupled to a cuff;

initializing an internal memory of a microcontroller;

entering a power saving mode;

actuating a power-on command from said key inputting means and automatically powering down in the absence of a subsequent input from said key inputting means within a predetermined time period after the actuation of said power-on command;

closing said solenoid valve in response to a subsequent input from said key inputting means within the predetermined time period;

pressurizing said cuff;

averaging pressure during pressurizing of said cuff and storing said average in said internal memory;

detecting pressure waves transmitted from an artery of a subject and storing electrical signals representative of said pressure waves in said internal memory;

increasing the pressurization of said cuff until a systolic pressure is detected;

calculating a systolic pressure and a diastolic pressure by exhausting air in said cuff;

displaying said systolic pressure, said diastolic pressure, and a heart rate;

exhausting the remaining air in said cuff; and turning off said sphygmomanometer.

6. A method of controlling a sphygmomanometer from a key inputting means for minute exhaustion comprising:

inserting a battery into said sphygmomanometer;

opening a solenoid valve coupled to a cuff;

initializing an internal memory of a microcontroller;

entering a power saving mode;

actuating a power-on command from said key inputting means and automatically powering down in the absence of a subsequent input from said key inputting means within a predetermined time period after the actuation of said power-on command;

closing said solenoid valve in response to a subsequent input from said key inputting means within the predetermined time period;

pressurizing said cuff;

terminating the pressurization of said cuff when the pressure reaches a systolic pressure;

computing initial values for opening and closing times of said solenoid valve for minute exhaustion;

exhausting the air in said cuff by opening and closing said solenoid valve in accordance with said computation;

correcting said opening and closing times of said solenoid valve by a linear prediction;

detecting and storing in internal memory data representative of the pressure of said cuff;

calculating a systolic pressure and a diastolic pressure from said data;

displaying said systolic pressure and diastolic pressure;

exhausting the remaining air in said cuff by opening said solenoid valve; and turning off said sphygmomanometer.

7. A sphygmomanometer for controlling minute exhaustion, comprising:

a cuff for compressing an upper arm of a subject;

air pumping means for pumping air into said cuff;

a solenoid valve for exhausting the air from said cuff;

a sensor for converting pressure caused by the air in said cuff to an electrical signal, said pressure being representative of a pressure exerted on said cuff by an artery of the arm;

a microcontroller comprising means for operating said air pumping means based on said pressure until at least a systolic pressure is reached, means for computing closing and opening times of said solenoid valve by linear prediction based on a previous quantity of air exhausted from said cuff, means for controlling said solenoid valve in accordance with said computed closing and opening times so that the air from said cuff is exhausted minutely, and means for computing a blood pressure in response to said electrical signal from said sensor;

a display connected to said microcontroller for displaying the calculated blood pressure;

a key inputting means for controlling said microcontroller; and wherein said microcontroller further comprises means for reducing power consumption in the microcontroller in response to a predetermined time period between actuation of said key inputting means.

8. A sphygmomanometer for controlling minute exhaustion, comprising:

a cuff for compressing an upper arm of a subject;

air pumping means for pumping air into said cuff;

a solenoid valve for exhausting the air from said cuff;

a sensor for converting pressure caused by the air in said cuff to an electrical signal, said pressure being representative of a pressure exerted on said cuff by an artery of the arm;

a microcontroller comprising means for operating said air pumping means based on said pressure until at least a systolic pressure is reached, means for computing closing and opening times of said solenoid valve by linear prediction based on a previous quantity of air exhausted from said cuff, means for controlling said solenoid valve in accordance with said computed closing and opening times so that the air from said cuff is exhausted minutely, and means for computing a blood pressure in response to said electrical signal from said sensor;

a key inputting means for controlling said microcontroller; and wherein said microcontroller further comprises means for reducing power consumption in the microcontroller in response to a predetermined time period between actuation of said key inputting means.

* * * * *

UNITED STATES PATENT AND TRADEMARK OFFICE
CERTIFICATE OF CORRECTION

PATENT NO.   : 5,662,092
DATED        : September 2, 1997
INVENTOR(S)  : Tae-Young Choi; Si-Chul Lee; Yong-Bum Kim It is certified that error appears in the above-indentified patent and that said Letters Patent is hereby corrected as shown below:

On the title page;
Item [30], Foreign Application Priority Data, replace
"Jul. 27, 1979 [KE]   Kenya....94-18259" with
-- Jul. 27, 1979 [KR]   Korea....94-18259 --.
Column 1, line 27, replace "of a the" with -- of the --.
Column 1, line 65, change "depressurized" to -- depressurize --.
Column 4, line 13, change "(nor shown)" to -- not shown --.
Column 5, line 9, change "during" to -- During --.
Column 5, line 55, change "an second" to -- a second --.
Column 6, line 8, after "may" insert -- be --.
Column 6, line 8, change "microcontroller." to -- microcontroller, --.
Column 6, line 14, change "closed" to -- close --.
Column 6, line 20, change "turing" to -- turning --.
Column 6, line 57, change "closed" to -- close --.
Column 7, line 53, delete "as illustrative" (second occurrence).
Column 7, line 55, change "than" to -- in --.

Signed and Sealed this

Twenty-fifth Day of August, 1998

*Attest:*

BRUCE LEHMAN

*Attesting Officer*   *Commissioner of Patents and Trademarks*